United States Patent [19]

Vértesy et al.

[11] Patent Number: 5,149,716
[45] Date of Patent: Sep. 22, 1992

[54] INSULIN DERIVATIVES, PROCESS FOR THEIR PREPARATION, THEIR USE AND A PHARMACEUTICAL PREPARATION CONTAINING THEM

[75] Inventors: László Vértesy, Eppstein/Taunus; Karl Geisen, Frankfurt am Main; Richard Bicker, Liederbach, all of Fed. Rep. of Germany

[73] Assignee: Hoechst Aktiengesellschaft, Frankfurt am Main, Fed. Rep. of Germany

[21] Appl. No.: 603,835

[22] Filed: Oct. 26, 1990

[30] Foreign Application Priority Data

Nov. 6, 1989 [DE] Fed. Rep. of Germany ....... 3936876

[51] Int. Cl.$^5$ ...................... A61K 37/26; A61K 37/02
[52] U.S. Cl. .......................................... 514/3; 514/4; 530/303
[58] Field of Search ......................... 514/3, 4; 530/303

[56] References Cited

U.S. PATENT DOCUMENTS 4,608,364  8/1986  Grau ........................................ 514/4
4,701,440 10/1987  Grau .

FOREIGN PATENT DOCUMENTS

| 54495/86 | 9/1986 | Australia . |
| 75916/87 | 1/1988 | Australia . |
| 15559/88 | 11/1988 | Australia . |
| 47332/89 | 7/1990 | Australia . |
| 0140084 | 9/1984 | European Pat. Off. . |
| 0194864 | 9/1986 | European Pat. Off. . |
| 0132770 | 9/1987 | European Pat. Off. . |
| 0132769 | 1/1988 | European Pat. Off. . |
| 0254516 | 1/1988 | European Pat. Off. . |
| 0376156 | 12/1988 | European Pat. Off. . |
| 3327928 | 2/1985 | Fed. Rep. of Germany . |
| 3837273 | 5/1990 | Fed. Rep. of Germany . |
| 3844211 | 7/1990 | Fed. Rep. of Germany . |

OTHER PUBLICATIONS

CA 93: 198218P (1980) Roesen et al.
Rosen et al. *Biochem J* vol. 186 (1980) 945–952.
Rose et al., *Advances In Protein Chemistry* vol. 37 25–31 (1985).
*Advances in Protein Chemistry,* Anfinsen et al., Academic Press, pp. 340–347 (1972).
*Biochemistry,* Lehninger, Worth Publishers Inc., pp. 71–76 (1977).

*Primary Examiner*—Merrell C. Cashion, Jr.
*Assistant Examiner*—B. Celsa
*Attorney, Agent, or Firm*—Finnegan, Henderson Farabow, Garrett and Dunner

[57] ABSTRACT

The invention relates to insulin derivatives of the formula III $$R^{4-1}-\text{Arg}-\boxed{\text{Gly} \quad \text{A chain} \quad \text{Asn}}-\text{OH}$$
$$\text{A0} \quad \text{A1} \quad \overset{\text{S--S}}{\phantom{xx}} \quad \text{A21}$$

$$H-\boxed{\text{Phe} \quad \text{B chain} \quad \text{Lys}}-R^{30}-R^{31}$$
$$\text{B1} \quad \phantom{xx} \quad \text{B29}$$

(with S—S bridges between A chain and B chain)

in which $R^{30}$ and $R^{31}$ together are OH, or $R^{30}$ is a radical of a neutral, genetically encodable L-amino acid and $R^{31}$ is OH or a physiologically acceptable organic group of basic character having up to 50 carbon atoms, whose synthesis involves 0 to 3 α-amino acids and whose optional terminal carboxyl function can be present free, as an ester function, as an amide function, as a lactone or reduced to $CH_2OH$, and $R^{4-1}$ is a radical of a genetically encodable L-amino acid, and physiologically acceptable salts of said insulin derivative of the formula III.

9 Claims, No Drawings

INSULIN DERIVATIVES, PROCESS FOR THEIR PREPARATION, THEIR USE AND A PHARMACEUTICAL PREPARATION CONTAINING THEM

DESCRIPTION

As is known, insulin and insulin derivatives are required in considerable amounts for the treatment of the disease diabetes mellitus and are partly also produced on a large scale. In spite of the considerable number of already-existing insulin preparations and modifications having different profiles of action, owing to the diversity of organisms with their inter- and intra-individual variations a need still exists for other insulin products having, in turn, other properties and characteristics of action.

Insulin derivatives having a sustained action are described, for example, in European Patent 132,769 and European Patent 132,770. They are derivatives which are specifically basically modified in position B31 of the insulin B chain, of the following formula I:

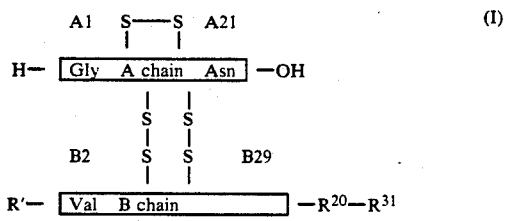

in which
$R^1$ is H or H-Phe,
$R^{30}$ is the radical of a neutral, genetically encodable L-amino acid and
$R^{31}$ is a physiologically acceptable organic group of basic character having up to 50 carbon atoms, whose synthesis involves 0 to 3 α-amino acids and whose optional terminal carboxyl function can be present free, as an ester function, as an amide function, as a lactone or reduced to $CH_2OH$.

An isoelectric point between 5.8 and 8.5 (measured by isoelectric focusing) is characteristic of these insulin derivatives. The isoelectric point—displaced into the neutral range compared to the isoelectric point of the unmodified native insulin or proinsulin (at pH=5.4)—is due to the additional positive charge(s) situated on the surface of the molecule as a result of the basic modification. These basically modified insulin derivatives are thus less soluble in the physiologically important neutral range than, for example, native insulin or proinsulin which are normally dissolved in the neutral range.

The sustained or depot action of the basically modified insulin derivatives of the formula I has its origin in the poor solubility at the isoelectric point. According to the two abovementioned publications, the redissolution of the insulin derivatives under physiological conditions ought to be achieved by elimination of the additional basic groups, which is achieved, depending on the derivative, by tryptic or trypsin-like and/or carboxypeptidase B or carboxypeptidase B-like and/or esterase activity. The groups eliminated in each case are either pure physiological metabolites or else easily metabolizable, physiologically acceptable substances.

The abovementioned depot principle as a result of basic modification of the insulin was further used in the following period by means of the preparation and corresponding use of other basically modified insulin derivatives - principally within the A and B chains; cf., for example, European Patent Application 0,194,864 and European Patent Application 0,254,516.

A few basically modified insulin derivatives are also known in which the basic modification is located in the lengthening of the A chain beyond the position A1; cf. P. Rösen et al., Biochem. J. (1980) Vol. 186, 945–952. Such insulin derivatives having basic amino acids as modification components and specifically described in this reference are:

Lys-Arg-Gly$^{A1}$ bovine insulin,
Arg-Gly$^{A1}$ bovine insulin,
Arg-Arg-Gly$^{A1}$ bovine insulin and Arg-Arg-Arg-Gly$^{A1}$ bovine insulin.

These insulin derivatives ought to have a considerably reduced biological activity compared to unmodified insulin; cf. in particular Table 1 on p. 947 of the said reference. Nothing is stated in the reference about a possible depot effect of the compounds.

Particularly advantageous, basically modified insulin derivatives having a depot effect are the basically modified insulin derivatives according to German Patent Application P 38 44 211.6 of 29.12.1988; they are insulin derivatives of the formula II below, in the AO position of which is the basic amino acid arginine:

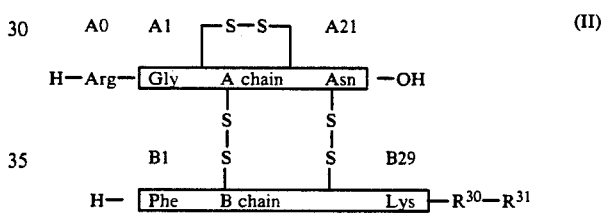

in which
a) $R^{30}+R^{31}$ together=OH or
$R^{30}$=a radical or a neutral, genetically encodable L-amino acid and $R^{32}$=OH or a physiologically acceptable organic group of basic character having up to 50 carbon atoms, whose synthesis involves 0 to 3 α-amino acids and whose optional terminal carboxyl function can be present free, as an ester function, as an amide function, as a lactone or reduced to $CH_2OH$,
with the exception of the case in which, at the same time, $R^{30}$=Ala, $R^{31}$=OH and the A and B chains are the sequences of bovine insulin (i.e. AO-Arg bovine insulin).

The physiologically tolerable salts (such as, for example, the alkali metal or ammonium salts) of these insulin derivatives are equivalent to the free insulin derivatives.

These insulin derivatives have, as a result of their basic modification in the AO position—as well as the previously mentioned basically modified insulin derivatives—a sustained action profile and—compared to the previously mentioned basically modified insulin derivatives—distinct advantages in relation to the tolerability in the organism; their biological activity corresponds to that of native insulin.

In the attempt to develop these insulin derivatives still further, it has now been found that this aim is achieved by a lengthening of the A chain beyond the AO-Arg position.

The invention therefore relates to novel insulin derivatives of the formula III

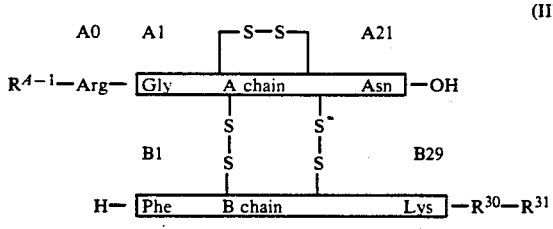

(III)

in which
a) $R^{30}+R^{31}$ together$=$OH or
b) $R^{30}=$a radical of a neutral, genetically encodable L-amino acid and $R^{31}=$OH or a physiologically acceptable organic group of basic character having up to 50 carbon atoms, whose synthesis involves 0 to 3 α-amino acids and whose optional terminal carboxyl function can be present free, as an ester function, as an amide function, as a lactone or reduced to $CH_2OH$, and
c) $R^{A-1}=$a radical of a genetically encodable L-amino acid or a physiologically acceptable organic group having up to 50 carbon atoms,
with the exception of the cases in which, at the same time, $R^{30}=$Ala, $R^{31}=$OH, $R^{A-1}=$Lys or Arg and the A and B chain are the sequences of bovine insulin, and their physiologically tolerable salts.

a) The compounds of the formula III where $R^{30}+R^{31}$ together$=$OH are the corresponding $R^{A-1}$—A0—Arg—Des—B30 insulins; these compounds are particularly preferred.

b) Alternatively, in formula III $R^{30}$ can also be the radical of a neutral, genetically encodable L-amino acid and $R^{31}=$OH or a corresponding physiologically acceptable organic group of basis character having up to 50 carbon atoms; these compounds are corresponding $R^{A-1}$—AO—Arg insulin derivatives.

$R^{30}$ and $R^{31}$ have the same meaning as in formula II for the compounds according to the abovementioned earlier patent application.

Neutral, genetically encodable L-amino acids—for $R^{30}$—are Gly, Ala, Ser, Thr, Val, Leu, Ile, Asn, Gln, Cys, Met, Tyr, Phe and Pro; preferred among these are Ala, Thr and Ser, in particular only Thr.

If $R^{31}=$OH, insulin derivatives result which differ from the corresponding insulins only by the modification in the (A-1) and AO position.

If $R^{31}=$a corresponding physiologically acceptable organic group of basic character having up to 50 carbon atoms, insulin derivatives result which likewise only differ from the basically modified insulin derivatives according to the publications European Patent 132,769 and European Patent 132,770 mentioned at the beginning by the modification in the positions (A-1) and AO.

If no α-amino acids are involved in the synthesis of $R^{31}$, the following basic groups, for example, are suitable for this radical:

Amino-$(C_2-C_6-)$-alkoxy, $C_1-C_4)$-alkylamino-$(C_2-C_6)$-alkoxy, di-$(C_1-C_4)$-alkylamino-$(C_2-C_6)$-alkoxy, tri-$(C_1-C_4)$-ammonio-$(C_2-C_6)$-alkoxy, amino-$(C_2-C_6)$-alkylamino, [$(C_1-C_4)$-alkyl-amino]-$(C_2-C_6)$-alkylamino, di-$(C_1-C_4)$-alkylamino-$(C_2-C_6)$-alkylamino or [tri-$(C_1-C_4)$-alkylamino]-$(C_2-C_6)$-alkylamino, in particular —O—$[CH_2]_p$-$NR_2$, —O—$[CH_2]_p$-$N^{\oplus}R_3$, —NH—$[CH_2]_p$-$NR_2$ or —NH—$[CH_2]_p$-$N^{\oplus}R_3$, wherein $p=2$ to 6 and R is identical or different and is hydrogen or $(C_1-C_4)$-alkyl.

If up to 3 α-amino acids are involved in the synthesis of $R^{31}$, these are primarily neutral or basic, naturally occurring L-amino acids and/or the D-amino acids corresponding to these. Neutral, naturally occurring amino acids are in particular Gly, Ala, Ser, Thr, Val, Leu, Ile, Asn, Gln, Cys, Met, Tyr, Phe, Pro and Hyp. Basic, naturally occurring amino acids are, in particular, Arg, Lys, Hyl, Orn, Cit and His. If only neutral α-amino acids are involved—in order that $R^{31}$ has basic character—their terminal carboxyl function cannot be free; the carboxyl function must rather be esterified or amidated in this case with a basic group, in which case suitable basic groups—in the case in which no α-amino acids are involved in the synthesis of $R^{31}$—are, for example, the previously mentioned groups. Of course, these basic ester or amide groups may also block the carboxyl function of basic α-amino acids. Neutral ester or amide groups such as, for example $(C_1-C_6)$-alkoxy, $(C_3-C_6)$-cycloalkyloxy, $NH_2$, $(C_1-C_6)$-alkylamino or di-$(C_1-C_6)$-alkylamino may also be suitable for blocking the carboxyl function of the basic α-amino acids—if blocking is desired.

Of course, the terminal carboxyl function can only be present as a lactone if the terminal amino acid is a hydroxyamino acid.

Moreover, the terminal carboxyl function can also be reduced to $CH_2OH$.

$R^{A-1}$ can be the radical of any of the (20) genetically encodable amino acids. The genetically encodable amino acids are:

Gly, Ala, Ser, Thr, Val, Leu, Ile, Asp, Asn, Glu, Gln, Cys, Met, Arg, Lys, His, Tyr, Phe, Trp, Pro.

Furthermore, $R^{A-1}$ can also be a physiologically acceptable organic group having up to 50 carbon atoms; such groups are, for example, straight-chain or branched alkyl groups, or aryl or aralkyl groups which may also optionally be substituted, for example, by hydroxyl, amino, alkoxy, carboxyl, carboalkoxy and/or carboxamide groups.

Preferably, $R^{A-1}$ is Ala, Thr, Ser, Lys or Arg, in particular only Thr.

Preferred insulin derivatives of the formula III are those where
a) $R^{30}+R^{31}=$OH or
b) $R^{30}=$a radical of Ala, Thr or Ser, in particular of Thr, and $R^{31}=$OH, and
c) $R^{A-1}=$Thr.

These insulin derivatives are (A-1)Thr—(AO)Arg—Des(B30) insulins and (A-1)Thr-(AO)Arg insulins.

If the A1 to A21 and the B1 to B29 sequences here are the (identical) sequences of human, porcine or rabbit insulin or the (in this respect slightly different) sequences of bovine insulin, these are (A-1)Thr(AO)Arg—Des-(B30) human, porcine, rabbit or bovine insulin, and (A-1)Thr—(AO) Arg human insulin [with (B30)Thr], (A-1)Thr—(AO)Arg porcine insulin [with (B30)Ala], (A-1)Thr—(AO)Arg rabbit insulin [with (B30)Ser] and (A-1)Thr—(AO)Arg bovine insulin [with (B30)Ala].

Particularly preferred insulin derivatives of the formula III are those where
a) $R^{30}+R^{31}=$OH and
b) $R^{A-1}=$Thr, i.e. the (A-1)Thr—(AO)Arg—Des-(B30) insulins, in particular the (A-1)Thr—(AO)Arg—Des(B30) human insulin.

The A chain and the B1 to B29 chain in formula III can in principle be the sequences of all possible insulins; however, they are preferably the sequences of human, porcine, rabbit or bovine insulin, in particular the sequences of human insulin (which are identical with the A1 to A21 and B1 to B29 sequences of porcine and rabbit insulin).

The isoelectric point of the insulin derivatives of the formula III is between 5.5 and 9.0 (measured by isoelectric focusing).

The preparation of the insulin derivatives of the formula III can be carried out by a) bringing an insulin derivative of the formula IV

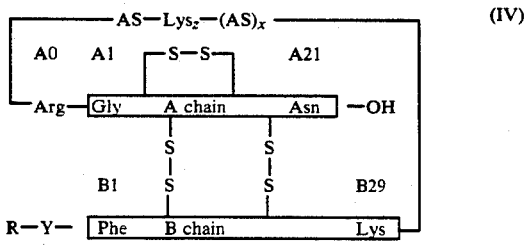

in which
AS = genetically encodable amino acid(s),
x, z = independently of one another 0 or integers from 1–50, where, however—if x≠0—also z≠0,
R = an organic radical having up to 50 carbon atoms, preferably a radical of a genetically encodable amino acid or a peptide radical formed from two or more identical or different genetically encodable amino acids,
y = Lys or Arg,
and the A and B (1 to 29) chains preferably have the sequences of human, porcine, rabbit or bovine insulin, in particular of human, porcine or rabbit insulin, into contact with lysyl endopeptidase, the bonds at the C-terminal end of the lysyl radicals being cleaved, and—if Y = Lys—the compounds of the formula III where $R^{30}+R^{31}$ together = OH and $R^{4-1}$ = genetically encodable amino acid being obtained, or—if Y = Arg—trypsin or a trypsin-like endopeptidase still being added, the pre-amino acid sequence R-Arg being cleaved from the B chain and a compound of the formula III where $R^{30}+R^{31}$ together = OH and $R^{4-1}$ = genetically encodable amino acid like-wise being formed, or by b) reacting an optionally protected insulin product of the formula V

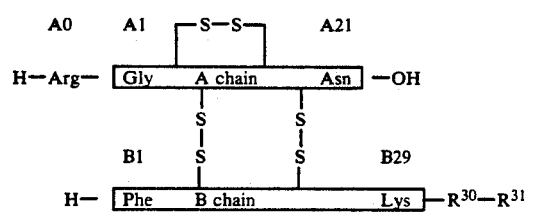

in which $R^{30}$ and $R^{31}$ have the same meaning as in formula III, at the N-terminus of the (AO) arginine in a manner known per se with optionally protected and/or activated, genetically encodable L-amino acids, or with donors of physiologically acceptable organic radicals having up to 50 carbon atoms, preferably of—optionally substituted—alkyl, aryl or alkaryl radicals having not more than 50 carbon atoms and then removing the protective groups present in a known manner.

The starting products of process variant a)—the insulin precursors of the formula IV—are preferably obtained by genetic engineering methods, such as are described, for example, in German Patent Applications P 38 21 159.9 (of 23.06.1988) and P 38 37 273.8 (of 03.11.1988) and the German Patent Application P 38 44 211.6 (of 29.11.1988) already mentioned previously.

If, in the insulin precursors of the formula IV, Y = -Lys, the enzymatic cleavage by means of lysyl endopeptidase proceeds directly to give the corresponding Des-B30 final products of the formula III (where $R^{30}+R^{31}$ together = OH, and $R^{4-1}$ = genetically encodable amino acid); if Y = Arg, the radical R—Y still remains at the N-terminal end of the B chain in the cleavage by means of lysyl endopeptidase (since lysyl endopeptidase only cleaves peptide chains on the carboxyl side or Lys). This radical is then preferably additionally removed by means of trypsin, a substrate/enzyme ratio of about (100–100,000):1, in particular of about (1000–10,000):1 being expedient. The same final product results as in the case of the starting material where Y = Lys. Otherwise, the enzymatic cleavages are carried out in a manner known per se and preferably at room temperature.

The starting materials for process variant b)—the insulin products of the formula V—are the AO—Arg insulin derivatives described in the German Patent Application P 38 44 211.6 (of 29.11.1988). They can still be provided with protective groups—customary in peptide chemistry—for the amino and/or carboxyl groups for use in process variant b), in which case, of course, the N-terminus of the AO arginine must remain unprotected (since the coupling of the radical $R^{4-1}$ has to take place there). The insulin products of the formula V—optionally appropriately protected—are then reacted with genetically encodable amino acids—likewise optionally protected and/or activated—or with donors of physiologically acceptable organic radicals having up to 50 carbon atoms, preferably of optionally substituted alkyl, aryl or aralkyl radicals (for example alkyl, aryl or aralkyl halides) having up to 50 carbon atoms in a manner customary for reactions of this type; some suitable substituents for the alkyl, aryl and aralkyl radicals are those which have previously been described in the explanation of the radical $R^{4-1}$.

The protective groups which may be present are then removed again in a manner known per se.

While according to process variant a) only insulin derivatives of the formula III where $R^{30}+R^{31}$ = OH (Des-B30 insulin derivatives) and $R^{4-1}$ = radical of a genetically encodable amino acid can be obtained, the preparation of the insulin derivatives of the formula III having the radicals mentioned for $R^{30}$ and $R^{31}$ in the legend to formula III under b) and also the physiologically acceptable organic radicals having up to 50 carbon atoms for $R^{4-1}$ is also possible by process variant b).

The insulin derivatives of the formula III are fully active in vivo, which is extremely surprising with respect to the previously mentioned reference P. Rösen et al; they act very like the AO—Arg insulin derivatives described in the German Patent Application P 38 44 211.6. They are therefore used—like their physiologically tolerable salts (such as, for example, the Na or NH4 salts)primarily as active compounds for pharmaceutical preparations for the treatment of diabetes mellitus.

The invention therefore also relates to a pharmaceutical preparation which comprises at least one insuli derivative of the formula III and/or at least one of its physiologically tolerable salts in dissolved, amorphous and/or crystalline form - preferably in amorphous and/or crystalline form.

Preferred insulin derivatives of the formula III for this pharmaceutical preparation are
(A-1)-Thr—AO—Arg human insulin,
(A-1)Thr—AO—Arg porcine insulin,
(A-1)Thr—AO—Arg rabbit insulin,
(A-1)Thr—AO—Arg bovine insulin and
(A-1)Thr—AO—Arg—Des-B30 human insulin,
preferably only (A-1)Thr—AO—Arg—Des-B30 human insulin, and their physiologically tolerable salts.

The pharmaceutical preparation is preferably a solution or suspension for injection having a pH between about 3.0 and 9.0, preferably between about 5.0 and 8.5, which contains
a suitable isotonisizing agent,
a suitable preservative and, if desired, a suitable buffer, and, if desired, also a defined zinc ion concentration or
   another depot principle such as, for example, protamine sulfate,
all, of course, in sterile aqueous solution or suspension. The whole of the preparation components apart from the active compound form the preparation excipient.

Suitable isotonisizing agents are, for example, glycerol, glucose, mannitol, NaCl, or calcium or magnesium compounds such as, for example, $CaCl_2$, $MgCl_2$ etc.

Suitable preservatives are, for example, phenol, m-cresol, benzyl alcohol and/or p-hydroxybenzoic acid esters.

Buffer substances which can be used, in particular for establishing a pH between about 5.0 and 8.5, are, for example, sodium acetate, sodium citrate, sodium phosphate etc. Otherwise, physiologically acceptable dilute acids (typically HCl) or bases (typically NaOH) are also suitable for adjusting the pH.

If the preparation has a content of zinc, one of about 1 μg to 2 mg, in particular of about 5 μg to 200 μg of zinc/ml is preferred.

In order to vary the action profile of the preparation according to the invention, other modified (cf. European Patent 132,769 and European Patent 132,770 and German Patent Application P 38 44 211.6) and/or unmodified insulins, preferably bovine, porcine, rabbit or human insulin, in particular human insulin, can also be admixed.

Preferred active compound concentrations are those corresponding to about 1 to 15,000, further preferably about 5 to 1000 and in particular about 40 to 400 International Units/ml.

The pharmaceutical preparation is produced by bringing at least one insulin derivative of the formula III and/or at least one of its physiologically tolerable salts, if desired together with other modified and/or unmodified insulins or insulin derivatives, into a suitable presentation form using a physiologically acceptable excipient and, if desired, using suitable additives and auxiliaries.

The invention will now be illustrated in more detail by the following example.

Preparation of (A-1)Thr—(AO)Arg—Des—B30 human insulin by process variant a)

200 mg of the recombinant protein, prepared by the process according to German Patent Application P 38 21 159.9, of the formula:

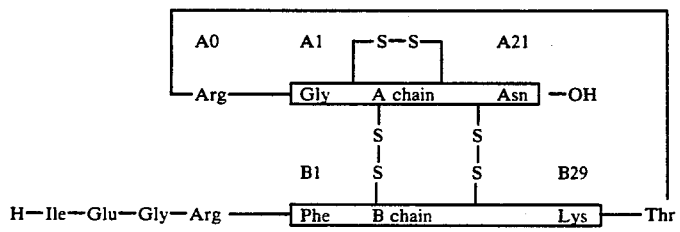

i.e. a compound of the formula V in which AS=Thr, x,z=0, Y=Arg and R=H—Ile—Glu—Gly—were dissolved in 50 ml of 20 mM phosphate buffer, pH 8.4, and digested at 20° C. for 30 minutes with 100 mcg of lysyl endopeptidase. The peptide sequence Ile—Glu—Gly—Arg was then removed with 100 mcg of trypsin. After a reaction time of 2 hours at room temperature, the reaction of the batch was stopped by addition of trifluoroacetic acid and the reaction product was purified on reverse phase in a 0.1% trifluoroacetic acid/acetonitrile system. 51 mg of (A-1)Thr—(AO)Arg—(B30)Des—Thr human insulin were formed of the formula:

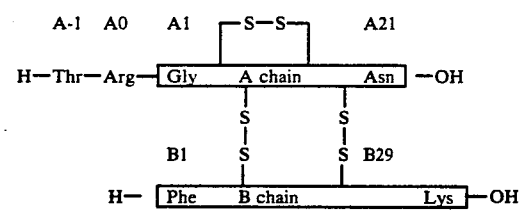

Hypoglycemic action 2.2 mg of anhydrous (A-1)Thr—(AO)Arg—(B30)Des—Thr human insulin were taken up in 1.5 ml of 0.9% strength NaCl solution. 2.2 mg of human insulin, also in 1.5 ml of physiological saline solution, were used as comparison and standard substance. 6.25 microliters of sample solution/kg of live weight were in each case intravenously administered to 5 fasting male rabbits having mean weights of 3.1 kg. 6.25 microliters of standard solution per kg were likewise administered i.v. to 5 other animals. After various times, blood samples were taken and examined for blood sugar concentrations. Within the limits of error, the following measurement results were found:

|  | Blood glucose in % of the starting value after | | | | |
|---|---|---|---|---|---|
|  | ½ h | 1 h | 2 h | 3 h | 4 h |
| Standard solution (human insulin) | −28 | −27 | −18 | −11 | −6 |
| (A-1)Thr-(AO)-Arg-(B30)Des-Thr insulin | −31 | −31 | −20 | −3 | ±0 |

From the numerical values, it can be seen that the hypoglycemic action of the novel insulin derivative is of the same order of magnitude as that of the (unmodified) human insulin.

On subcutaneous administration of a crystal suspension, the novel insulin derivative acts in a sustained manner.

We claim:

1. An insulin derivative of the formula III

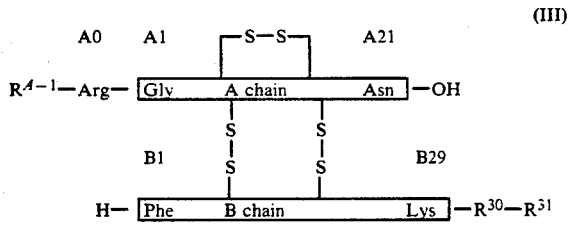

in which
a) $R^{30} + R^{31}$ together = OH, or
b) $R^{30}$ = a radical or a neutral, genetically encodable L-amino acid and
$R^{31}$ = OH, or
a physiologically acceptable organic group of basic character having up to 50 carbon atoms, whose synthesis involves 0 to 3 α-amino acids and whose optional terminal carboxyl function can be present free, as an ester function, as an amide function, as a lactone, or reduced to $CH_2OH$, and
c) $R^{A-1}$ = a radical of Thr, Ser, or Ala, and physiologically acceptable salts thereof, with the exception of the cases in which, at the same time, $R^{30}$ = Ala, $R^{31}$ = OH, $R^{A-1}$ = Lys or Arg, and the A and B chains are the sequences of bovine insulin.

2. The insulin derivative and its physiologically tolerable salts of claim 1, wherein, in formula III
a) $R^{30} + R^{31}$ = OH or
b) $R^{30}$ = a radical of Ala, Thr or Ser, in particular of Thr, and $R^{31}$ = OH, and
c) $R^{A-1}$ = Thr.

3. The insulin derivative and its physiologically tolerable salts of claim 1, wherein, in formula III
a) $R^{30} + R^{31}$ = OH and c) $R^{A-1}$ = Thr.

4. The insulin derivative and its physiologically tolerable salts of claim 1,
wherein, in formula III, the A chain and the B chain (B1-B29) are the sequences of human, porcine, rabbit or bovine insulin, preferably of human, porcine or rabbit insulin.

5. The insulin derivative of claim 1, which has an isoelectric point between 5.5 and 9.0.

6. A method which comprises using the insulin derivatives and their physiologically tolerable salts of claim 1 as active compounds for pharmaceutical preparations for the treatment of diabetes mellitus.

7. A pharmaceutical preparation which comprises at least one insulin derivative of the formula III and/or at least one of its physiologically tolerable salts of claim 1 in dissolved, amorphous and/or crystalline form—preferably in amorphous and/or crystalline form.

8. The pharmaceutical preparation of claim 7, which comprises at least one of the following insulin derivatives - coming under the formula III:
(A-1)Thr—AO—Arg human insulin,
(A-1)Thr—AO—Arg porcine insulin,
(A-1)Thr—AO—Arg rabbit insulin,
(A-1)Thr—AO—Arg bovine insulin and
(A-1)Thr—AO—Arg-Des-B30 human insulin,
preferably only (A-1)Thr—AO—Arg—Des-B30 human insulin, and their physiologically tolerable salts.

9. The pharmaceutical preparation of claim 7 as an injection solution or suspension having a pH between about 3.0 and 9.0, preferably about 5.0 and 8.5.

* * * * *

UNITED STATES PATENT AND TRADEMARK OFFICE
CERTIFICATE OF CORRECTION

PATENT NO. : 5,149,716
DATED : September 22, 1992
INVENTOR(S) : Laszlo Vertesy et al.

It is certified that error appears in the above-identified patent and that said Letters Patent is hereby corrected as shown below:

Claim 1, column 9, line 34, after "radical" change "or" to --of--.

Signed and Sealed this

Fifteenth Day of February, 1994

BRUCE LEHMAN

Attest:

Attesting Officer

Commissioner of Patents and Trademarks